United States Patent [19]

Guillaumet et al.

[11] Patent Number: 5,077,408

[45] Date of Patent: Dec. 31, 1991

[54] PROCESS FOR THE SYNTHESIS OF OXAZOLOPYRIDINE COMPOUNDS

[75] Inventors: Gérald Guillaumet; Christine Flouzat, both of Orleans, France

[73] Assignee: Science et Organisation, Neuilly-sur-Seine, France

[21] Appl. No.: 583,281

[22] Filed: Sep. 17, 1990

[30] Foreign Application Priority Data

Sep. 20, 1989 [FR] France ............................. 89 12324

[51] Int. Cl.$^5$ ............................................. C07D 498/04
[52] U.S. Cl. ..................................... 546/116; 546/115
[58] Field of Search .................................. 546/115, 116

[56] References Cited

U.S. PATENT DOCUMENTS 4,038,396 7/1977 Shen et al. ............................ 546/115

OTHER PUBLICATIONS

Couture et al., Heterocycles, 22(6), pp. 1383–1385 (1984).
Yamamoto et al., Chemistry Letters, pp. 1225–1228 (1982).

Primary Examiner—Bernard Dentz
Attorney, Agent, or Firm—Gordon W. Hueschen

[57] ABSTRACT

Process for the synthesis of compounds of formula (I):

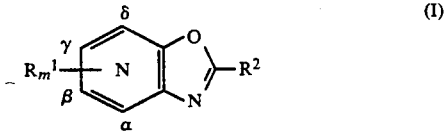

their pyridinium salts and N-oxides, in which formula:
the nitrogen of the pyridine ring is situated in the α-, β-, γ- or δ-position with respect to the ring junction;
$R^1$ represents a halogen, a substituted or unsubstituted alkyl, a substituted or unsubstituted alkoxy or a nitro, substituted or unsubstituted amino, phenyl or cyano group;
$0 \leq m \leq 2$;
$R^2$ represents a lower alkyl or cycloalkyl group, a 5- or 6-membered heterocycle containing 1 or 2 hetero atoms, substituted or otherwise, or an aryl group

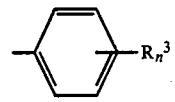

such that:
$R^3$ represents a halogen, a substituted or unsubstituted alkyl, a substituted or unsubstituted alkoxy or a nitro, phenyl, substituted or unsubstituted sulfonyl, cyano, thioalkyl, substituted or unsubstituted amino, substituted or unsubstituted sulfinyl, mercapto, hydroxyl or ester group,
$0 \leq n \leq 5$
employing trimethylsilyl polyphosphate (PPSE) as a cyclization agent and enabling the compounds of formula (I) to be obtained in virtually quantitative yields. The compounds of formula I have anti-inflammatory, analgesic, and antipyretic activity.

17 Claims, No Drawings

PROCESS FOR THE SYNTHESIS OF OXAZOLOPYRIDINE COMPOUNDS

The present invention relates to a new process for the synthesis of oxazolopyridine compounds. More specifically, the present invention relates to a new process for the synthesis of compounds of general formula (I)

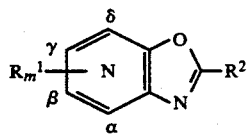

their pyridinium salts and N-oxides, in which formula:
the nitrogen of the pyridine ring is situated in the α-, β-, γ- or δ-position with respect to the ring junction;

$R^1$ represents:
- a halogen atom,
- a linear or branched lower alkyl group optionally substituted with one or more halogen atoms, such as a trifluoromethyl group,
- a linear or branched lower alkoxy group optionally substituted with one or more halogen atoms, such as a trifluoromethyl group,
- a nitro group,
- an amino group,
- a benzoylamino group,
- an amino group substituted with 1 or 2 identical or different lower alkyl groups,
- a carbonylamino group substituted with a lower alkoxy,
- a phenyl group,
- a cyano group;

$0 \leq M \leq 2$ $R^2$ represents:
a. a linear or branched lower alkyl group,
b. a linear or branched lower cycloalkyl group,
c. a 5- or 6-membered heterocycle containing 1 or 2 hetero atoms such as oxygen, nitrogen or sulfur, substituted or otherwise with a lower alkyl group or a cyano group,
d. an aryl group:

in which:
$0 \leq n \leq 5$
$R^3$ represents
- a halogen,
- a linear or branched lower alkyl group optionally substituted with one or more halogen atoms, such as a trifluoromethyl group,
- a linear or branched alkoxy group optionally substituted with one or more halogen atoms, such as a trifluoromethyl group,
- a nitro group,
- a phenyl group,
- a sulfonyl group substituted with a lower alkyl,
- a cyano group,
- a lower thioalkyl group,
- a carboxamide group,
- an amino group substituted with one or two identical or different lower alkyl groups,
- a sulfinyl group substituted with a lower alkyl,
- a mercapto group,
- a lower alkanoyloxy group,
- a hydroxyl group,
- a lower alkanoylamino group,
- an amino group,
- a benzoylamino group unsubstituted or substituted with a halogen such as a chlorine or a bromine or a lower alkyl or a lower alkoxy,

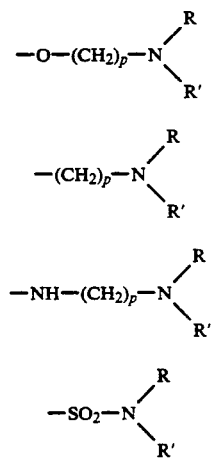

in which $1 \leq p \leq 3$, R, R', which may be identical or different, represent a hydrogen or a lower alkyl,
an ester group —$CO_2R$ in which R is a hydrogen or a lower alkyl,
—$(CH_2)_p$-$CO_2R$ with p and R defined as above,
—$(CH_2)_p$-CN with p defined as above,
two radicals $R^3$ on adjacent carbons linked to one another to form a methylenedioxy.

Lower alkyl, alkoxy, alkanoyloxy and alkanoylamino radicals are understood to mean groups containing 1 to 6 carbon atoms.

The compounds obtained are also useful as intermediates for the synthesis of acyloxazolopyridines.

A process for the synthesis of compounds of formula (I) has already been described in British Patent 1,421,619 and in the Journal of Medicinal Chemistry, 1978, 21, 11, 1158. These methods of synthesis enable the compounds of formula (I) to be obtained in overall yields generally of between 10 and 60%. The compounds of formula (I) are shown in these references to have anti-inflammatory, analgesic, and antipyretic activity.

The Applicant has now discovered a process for the synthesis of the compounds of formula (I) employing trimethylsilyl polyphosphate (PPSE) as a cyclization agent instead of polyphosphoric acid (PPA) frequently used, for example. This new method of synthesis, very simple to carry out, has proved especially advantageous since, surprisingly, it enables the compounds of formula (I) to be obtained in almost quantitative yields, hence markedly greater than those obtained hitherto.

More specifically, the process according to the present invention employs as a starting material a compound of formula (II):

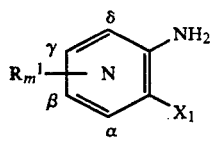

in which:

$X_1$ is a halogen, the nitrogen of the pyridine ring is situated in the a-, b-, c- or d-position with respect to the carbon bearing the halogen atom, $R_1$ and m have the same meaning as in the formula (I), which is treated with a compound of formula (III):

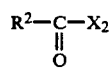

in which:

$X_2$ is a halogen, $R^2$ has the same meaning as in the formula (I), to lead to a compound of formula (IV):

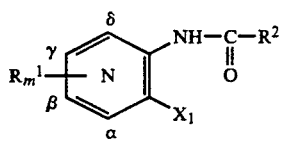

in which:

$X_1$ is a halogen, the nitrogen of the pyridine ring is situated in the $\alpha$-, $\beta$-, $\gamma$- or $\delta$-position with respect to the carbon bearing the halogen, $R^1$, $R^2$ and m have the same meaning as in the formula (I), a solution of which in a halogenated solvent is brought to reflux for a period preferably of between 10 and 24 hours, in the presence of trimethylsilyl polyphosphate (PPSE) preferably obtained at the time of use by refluxing phosphorus pentoxide in the presence of hexamethyldisiloxane in a halogenated solvent such as 1,2-dichlorobenzene under an inert atmosphere until a clear solution is obtained, to lead to the compounds of formula (I) which are purified, where appropriate, by recrystallization or chromatography.

The examples mentioned below illustrate the invention but in no way limit the latter.

A. PREPARATION OF THE TRIMETHYLSILYL POLYPHOSPHATE (PPSE) SOLUTION

This solution is used in the synthesis of the compounds of the invention.

2.5 g of phosphorus pentoxide (7 mmol) and 6.25 ml of hexamethyldisiloxane (33 mmol) are brought to reflux in 12.5 ml of 1,2-dichlorobenzene for approximately 5 minutes under an inert atmosphere ($N_2$, Ar) until a clear solution is obtained.

This solution is used without further treatment.

EXAMPLE 1: 2-PHENYLOXAZOLO[5,4-b]PYRIDINE

Stage A: 3-benzoylamino-2-chloropyridine 3.9 g (28 mmol) of benzoyl chloride are added to 30 ml of pyridine while the temperature is maintained at approximately $-5°$ C. A solution containing 3 g (23.3 mmol) of 3-amino-2-chloropyridine in 20 ml of pyridine is added to this solution using a pressure equalizing funnel. The reaction medium is left stirring overnight and then poured into a water/ice mixture. The solid obtained is then filtered off, washed several times with water and thereafter recrystallized in absolute ethanol.

Yield: 92%

Melting point: 89° C.

Stage B: 2-phenyloxazolo[5,4-b]pyridine 1.9 g (8 mmol) of 3-benzoylamino-2-chloropyridine, prepared in stage A, are added to the PPSE solution and then brought to reflux for 15 hours. The 1,2-dichlorobenzene is then evaporated off under vacuum. The residue is treated with a water/ice mixture. The pH of the solution is adjusted to 7–8 with 5% sodium bicarbonate solution. The precipitated product is filtered off and then recrystallized in cyclohexane.

Yield: 96%

Melting point: 101° C.

EXAMPLE 2: 2-(2-FLUOROPHENYL)OXAZOLO[5,4-b]PYRIDINE

Stage A: 3-(2-fluorobenzoylamino)-2-chloropyridine

Using the procedure described in Example 1, but replacing benzoyl chloride by 2-fluorobenzoyl chloride, 3-(2-fluorobenzoylamino)-2-chloropyridine is obtained.

Yield: 96%

Recrystallization solvent: isopropanol

Melting point: 122° C.

Stage B: 2-(2-fluorophenyl)oxazolo[5,4-b]pyridine

Using the procedure described in Example 1, but replacing 3-benzoylamino-2-chloropyridine by 3-(2-fluorobenzoylamino)-2-chloropyridine obtained in stage A.

Yield: 98%

Recrystallization solvent: ether/hexane

Melting point: 122° C.

EXAMPLE 3: 2-(4-CHLOROPHENYL)OXAZOLO[5,4-b]PYRIDINE

Stage A: 3-(4-chlorobenzoylamino)-2-chloropyridine

Using the procedure described in Example 1, but replacing benzoyl chloride by 4-chlorobenzoyl chloride, 3-(4-chlorobenzoylamino)-2-chloropyridine is obtained.

Yield: 95%

Recrystallization solvent: ethyl acetate/hexane

Melting point: 146° C.

Stage B: 2-(4-chlorophenyl)oxazolo[5,4-b]pyridine

Using the procedure described in Example 1, but replacing 3-benzoylamino-2-chloropyridine by 3-(4-chlorobenzoylamino)-2-chloropyridine obtained in stage A.

Yield: 97%

Recrystallization solvent: ethyl acetate/hexane
Melting point: 152° C.

EXAMPLE 4:
2-(2-CHLOROPHENYL)OXAZOLO[5,4-b]PYRIDINE

Stage A: 3-(2-chlorobenzoylamino)-2-chloropyridine

Using the procedure described in Example 1, but replacing benzoyl chloride by 2-chlorobenzoyl chloride, 3-(2-chlorobenzoylamino)-2-chloropyridine is obtained.
Yield: 96%
Recrystallization solvent: absolute ethanol
Melting point: 109° C.

Stage B: 2-(2-chlorophenyl)oxazolo[5,4-b]pyridine

Using the procedure described in Example 1, but replacing 3-benzoylamino-2-chloropyridine by 3-(2-chlorobenzoylamino)-2-chloropyridine obtained in stage A.
Yield: 85%
Recrystallization solvent: ethyl acetate/hexane
Melting point: 116° C.

EXAMPLE 5:
2-(4-METHOXYPHENYL)OXAZOLO[5,4-b]PYRIDINE

Stage A: 3 TM (4-methoxybenzoylamino)-2-chloropyridine

Using the procedure described in Example 1, but replacing benzoyl chloride by 4-methoxybenzoyl chloride, 3-(4-methoxybenzoylamino)-2-chloropyridine is obtained.
Yield: 96%
Recrystallization solvent: isopropanol
Melting point: 125° C.

Stage B: 2-(4-methoxyphenyl)oxazolo[5,4-b]pyridine

Using the procedure described in Example 1, but replacing 3-benzoylamino-2-chloropyridine by 3-(4-methoxybenzoylamino)-2-chloropyridine obtained in stage A.
Yield: 99%
Recrystallization solvent: hexane
Melting point: 144° C.

EXAMPLE 6:
2-(2-NITROPHENYL)OXAZOLO[5,4-b]PYRIDINE

Stage A: 3-(2-nitrobenzoylamino)-2-chloropyridine

Using the procedure described in Example 1, but replacing benzoyl chloride by 2-nitrobenzoyl chloride, 3-(2-nitrobenzoylamino)-2-chloropyridine is obtained.
Yield: 96%
Recrystallization solvent: absolute ethanol
Melting point: 160° C.

Stage B: 2-(2-nitrophenyl)oxazolo[5,4-b]pyridine

Using the procedure described in Example 1, but replacing 3-benzoylamino-2-chloropyridine by 3-(2-nitrobenzoylamino)-2-chloropyridine obtained in stage A.
Yield: 77%
Recrystallization solvent: ether/cyclohexane
Melting point: 125° C.

EXAMPLE 7:
2-(2-FURYL)OXAZOLO[5,4-b]PYRIDINE

Stage A: 3-(2-furoylamino)-2-chloropyridine

Using the procedure described in Example 1, but replacing benzoyl chloride by 2-furoyl chloride, 3-(2-furoylamino)-2-chloropyridine is obtained.
Yield: 75%
Recrystallization solvent: isopropanol
Melting point: 102° C.

Stage B: 2-(2-furyl)oxazolo[5,4-b]pyridine

Using the procedure described in Example 1, but replacing 3-benzoylamino-2-chloropyridine by 3-(2-furoylamino)-2-chloropyridine obtained in stage A.
Yield: 75%
Recrystallization solvent: cyclohexane
Melting point: 122° C.

EXAMPLE 8:
2-(4-TRIFLUOROMETHYLPHENYL)OXAZOLO[5,4-b]PYRIDINE

Stage A: 3-(4-trifluoromethylbenzoylamino)-2-chloropyridine

Using the procedure described in Example 1, but replacing benzoyl chloride by 4-trifluoromethylbenzoyl chloride, 3-(4-trifluoromethylbenzoylamino)-2-chloropyridine is obtained.

Stage B: 2-(4-trifluoromethylphenyl)oxazolo[5,4-b]pyridine

Using the procedure described in Example 1, but replacing 3-benzoylamino-2-chloropyridine by 3-(4-trifluoromethylbenzoylamino)-2-chloropyridine obtained in stage A.

EXAMPLE 9:
2-PHENYLOXAZOLO[4,5-b]PYRIDINE

Using the procedure described in Example 1, but replacing 3-amino-2-chloropyridine by 2-amino-3-chloropyridine.

EXAMPLE 10:
2-(2-FLUOROPHENYL)OXAZOLO[4,5-b]PYRIDINE

Using the procedure described in Example 2, but replacing 3-amino-2-chloropyridine by 2-amino-3-chloropyridine.

EXAMPLE 11:
2-(4-CHLOROPHENYL)OXAZOLO[4,5-b]PYRIDINE

Using the procedure described in Example 3, but replacing 3-amino-2-chloropyridine by 2-amino-3-chloropyridine.

EXAMPLE 12:
2-(2-CHLOROPHENYL)OXAZOLO[4,5-b]PYRIDINE

Using the procedure described in Example 4, but replacing 3-amino-2-chloropyridine by 2-amino-3-chloropyridine.

EXAMPLE 13:
2-(4-METHOXYPHENYL)OXAZOLO[4,5-b]PYRIDINE

Using the procedure described in Example 5, but replacing 3-amino-2-chloropyridine by 2-amino-3-chloropyridine.

EXAMPLE 14:
2-(2-NITROPHENYL)OXAZOLO[4,5-b]PYRIDINE

Using the procedure described in Example 6, but replacing 3-amino-2-chloropyridine by 2-amino-3-chloropyridine.

EXAMPLE 15:
2-(2-FURYL)OXAZOLO[4,5-b]PYRIDINE

Using the procedure described in Example 7, but replacing 3-amino-2-chloropyridine by 2-amino-3-chloropyridine.

EXAMPLE 16:
2-(4-TRIFLUOROMETHYLPHENYL)OXAZOLO[4,5-b]PYRIDINE

Using the procedure described in Example 8, but replacing 3-amino-2-chloropyridine by 2-amino-3-chloropyridine.

EXAMPLE 17:
2-PHENYLOXAZOLO[4,5-c]PYRIDINE

Using the procedure described in Example 1, but replacing 3-amino-2-chloropyridine by 3-amino-4-chloropyridine.

EXAMPLE 18:
2-(2-FLUOROPHENYL)OXAZOLO[4,5-c]PYRIDINE

Using the procedure described in Example 2, but replacing 3-amino-2-chloropyridine by 3-amino-4-chloropyridine.

EXAMPLE 19:
2-(4-CHLOROPHENYL)OXAZOLO[4,5-c]PYRIDINE

Using the procedure described in Example 3, but replacing 3-amino-2-chloropyridine by 3-amino-4-chloropyridine.

EXAMPLE 20:
2-(2-CHLOROPHENYL)OXAZOLO[4,5-c]PYRIDINE

Using the procedure described in Example 4, but replacing 3-amino-2-chloropyridine by 3-amino-4-chloropyridine.

EXAMPLE 21:
2-(4-METHOXYPHENYL)OXAZOLO[4,5-c]PYRIDINE

Using the procedure described in Example 5, but replacing 3-amino-2-chloropyridine by 3-amino-4-chloropyridine.

EXAMPLE 22:
2-(2-NITROPHENYL)OXAZOLO[4,5-c]PYRIDINE

Using the procedure described in Example 6, but replacing 3-amino-2-chloropyridine by 3-amino-4-chloropyridine.

EXAMPLE 23:
2-(2-FURYL)OXAZOLO[4,5-c]PYRIDINE

Using the procedure described in Example 7, but replacing 3-amino-2-chloropyridine by 3-amino-4-chloropyridine.

EXAMPLE 24:
2-(4-TRIFLUOROMETHYLPHENYL)OXAZOLO[4,5-c]PYRIDINE

Using the procedure described in Example 8, but replacing 3-amino-2-chloropyridine by 3-amino-4-chloropyridine.

EXAMPLE 25:
2-PHENYLOXAZOLO[5,4-c]PYRIDINE

Using the procedure described in Example 1, but replacing 3-amino-2-chloropyridine by 4-amino-3-chloropyridine.

EXAMPLE 26:
2-(2-FLUOROPHENYL)OXAZOLO[5,4-c]PYRIDINE

Using the procedure described in Example 2, but replacing 3-amino-2-chloropyridine by 4-amino-3-chloropyridine.

EXAMPLE 27:
2-(4-CHLOROPHENYL)OXAZOLO[5,4-c]PYRIDINE

Using the procedure described in Example 3, but replacing 3-amino-2-chloropyridine by 4-amino-3-chloropyridine.

EXAMPLE 28:
2-(2-CHLOROPHENYL)OXAZOLO[5,4-c]PYRIDINE

Using the procedure described in Example 4, but replacing 3-amino-2-chloropyridine by 4-amino-3-chloropyridine.

EXAMPLE 29:
2-(4-METHOXYPHENYL)OXAZOLO[5,4-c]PYRIDINE

Using the procedure described in Example 5, but replacing 3-amino-2-chloropyridine by 4-amino-3-chloropyridine.

EXAMPLE 30:
2-(2-NITROPHENYL)OXAZOLO[5,4-c]PYRIDINE

Using the procedure described in Example 6, but placing 3-amino-2-chloropyridine by 4-amino-3-chloropyridine.

EXAMPLE 31:
2-(2-FURYL)OXAZOLO[5,4-c]PYRIDINE

Using the procedure described in Example 7, but replacing 3-amino-2-chloropyridine by 4-amino-3-chloropyridine.

EXAMPLE 32:
2-(4-TRIFLUOROMETHYLPHENYL)OXAZOLO[5,4-c]PYRIDINE

Using the procedure described in Example 8, but replacing 3-amino-2-chloropyridine by 4-amino-3-chloropyridine.

EXAMPLE 33:
6-CHLORO-2-PHENYLOXAZOLO[4,5-b]PYRIDINE

Using the procedure described in Example 1, but placing 3-amino-2-chloropyridine by 2-amino-3,5-dichloropyridine.

EXAMPLE 34:
6-CHLORO-2-(2-FLUOROPHENYL)OXAZOLO[4,5-b]PYRIDINE

Using the procedure described in Example 2, but replacing 3-amino-2-chloropyridine by 2-amino-3,5-dichloropyridine.

EXAMPLE 35:
6-CHLORO-2-(4-CHLOROPHENYL)OXAZOLO[4,5-b]-PYRIDINE

Using the procedure described in Example 3, but replacing 3-amino-2-chloropyridine by 2-amino-3,5-dichloropyridine.

EXAMPLE 36:
6-CHLORO-2-(2-CHLOROPHENYL)OXAZOLO[4,5-b]PYRIDINE

Using the procedure described in Example 4, but replacing 3-amino-2-chloropyridine by 2-amino-3,5-dichloropyridine.

EXAMPLE 37:
6-CHLORO-2-(4-METHOXYPHENYL)OXAZOLO[4,5-b]PYRIDINE

Using the procedure described in Example 5, but replacing 3-amino-2-chloropyridine by 2-amino-3,5-dichloropyridine.

EXAMPLE 38:
6-CHLORO-2-(2-NITROPHENYL)OXAZOLO[4,5-b]PYRIDINE

Using the procedure described in Example 6, but replacing 3-amino-2 TM chloropyridine by 2-amino-3,5-dichloropyridine.

EXAMPLE 39:
6-CHLORO-2-(2-FURYL)OXAZOLO[4,5-b]PYRIDINE

Using the procedure described in Example 7, but replacing 3-amino-2-chloropyridine by 2-amino-3,5-dichloropyridine.

EXAMPLE 40:
6-CHLORO-2-(4-TRIFLUOROMETHYLPHENYL)OXAZOLO[4,5-b]PYRIDINE

Using the procedure described in Example 8, but replacing 3-amino-2-chloropyridine by 2-amino-3,5-dichloropyridine.

We claim:

1. A process for the synthesis of oxazolopyridine compounds of formula (I):

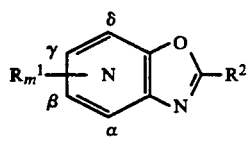

their pyridinium salts and N-oxides, in which formula:

the nitrogen of the pyridine ring is situated in the α-, β-, γ- or δ-position with respect to the ring junction;

$R^1$ represents:
  a halogen atom,
  a linear or branched lower alkyl group optionally substituted with one or more halogen atoms,
  a linear or branched lower alkoxy group optionally substituted with one or more halogen atoms,
  a nitro group,
  a amino group,
  a benzoylamino group,
  an amino group substituted with 1 or 2 identical or different lower alkyl groups,
  a carbonylamino group substituted with a lower alkoxy,
  a phenyl group,
  a cyano group;
$0 \leq m \leq 2$
$R^2$ represents:
  a. a linear or branched lower alkyl group,
  b. a linear or branched lower cycloalkyl group,
  c. a 5- or 6-membered heterocycle containing 1 or 2 hetero atoms
  d. an aryl group:

in which:
$0 \leq n \leq 5$
$R^3$ represents
  a halogen,
  a linear or branched lower alkyl group optionally substituted with one or more halogen atoms,
  a linear or branched lower alkoxy group optionally substituted with one or more halogen atoms,
  a nitro group,
  a phenyl group,
  a sulfonyl group substituted with a lower alkyl,
  a cyano group,
  a lower thioalkyl group,
  a carboxamide group,
  an amino group substituted with 1 or 2 identical or different lower alkyl groups,
  a sulfinyl group substituted with a lower alkyl,
  a mercapto group,
  a lower alkanoyloxy group,
  a hydroxyl group,
  a lower alkanoylamino group,
  an amino group,
  a benzoylamino group unsubstituted or substituted with a halogen or a lower alkyl or a lower alkoxy,

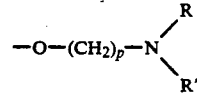

-continued

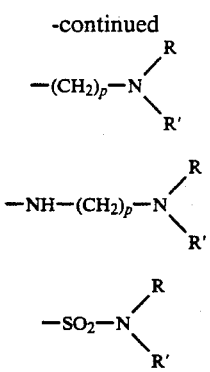

in which $1 \leq p \leq 3$, R, R', which may be identical or different, represent a hydrogen or a lower alkyl, an ester group -$CO_2R$ in which R is a hydrogen or a lower alkyl, -$(CH_2)_p$-$CO_2R$ with p and R defined as above, -$(CH_2)_p$-CN with p defined as above, two radicals $R^3$ on adjacent carbons linked to one another to form a methylenedioxy, wherein a compound of formula (II):

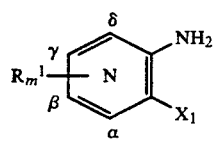
(II)

in which:

$X_1$ is a halogen, the nitrogen of the pyridine ring is situated in the α-, β-, γ- or δ-position with respect to the carbon bearing the halogen, $R^1$ and m have the same meaning as in the formula (I), is employed as a starting material, which compound is treated with a compound of formula (III):

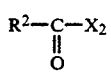
(III)

in which:

$X_2$ is a halogen, $R^2$ the same meaning as in the formula (I), to lead to a compound of formula (IV):

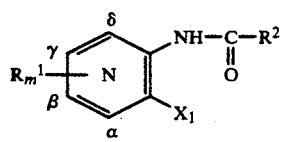
(IV)

in which:

$X_1$ is a halogen, the nitrogen of the pyridine ring is situated in the α-, β-, γ- or δ-position with respect to the carbon bearing the halogen, $R^1$, $R^2$ and m have the same meaning as in the formula (I), which is treated with a trimethylsilyl polyphosphate (PPSE) solution to lead to a compound of formula (I) which is purified, where appropriate, by recrystallization or chromatography.

2. The process for the synthesis of derivatives of formula (I) as claimed in claim 1, wherein the PPSE solution which is reacted with the compound of formula (IV) is a solution of PPSE in a halogenated solvent.

3. The process for the synthesis of derivatives of formula (I) as claimed in claim 2, wherein the PPSE solution which is reacted with the compound of formula (IV) is a solution of PPSE in a solvent selected from 1,2-dichlorobenzene and 1,2-dichloroethane.

4. The process for the synthesis of compounds of formula (I) as claimed in claim 1, wherein the compound of formula (IV) is treated with a PPSE solution under reflux.

5. The process for the synthesis of compounds of formula (I) as claimed in claim 1, wherein the compound of formula (IV) is treated with a PPSE solution under reflux for a period of between 10 and 24 hours.

6. The process for the synthesis of compounds of formula (I) as claimed in claim 1, wherein the PPSE solution which is reacted with the compound of formula (IV) is obtained at the time of use of refluxing phosphorus pentoxide in the presence of hexamethyldisiloxane.

7. The process as claimed in claim 1 using as starting material a compound of formula (II/A):

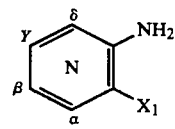
(II/A)

X in which 1 is halogen the nitrogen of the pyridinering is situated in the α, β, γ or δ position with respect to the carbon bearing the halogen, and a compound of formula (III):

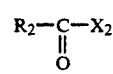

as defined in claim 1 enabling a compound of formula (I) for which m=0 to be obtained.

8. The process as claimed in claim 1 using as starting material as compound of formula (II):

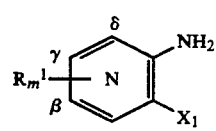
(II)

as defined in claim I, and a compound of formula (III/A):

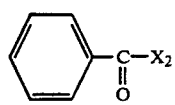
(III/A)

in which $X_2$ is a halogen, enabling a compound of formula (I) for which

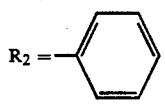

to be obtained.

9. The process as claimed in claim 1 using as starting material a compound of formula (II):

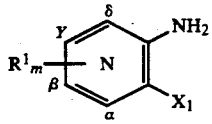

as defined in claim 1, and a compound of formula (III/B):

in which $R_3B$ is a halogen and $X_2$ is a halogen enabling a compound of formula (I) for which

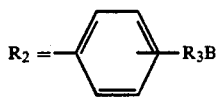

in which $R_3B$ is a halogen to be obtained.

10. The process as claimed in claim 1, using as starting material a compound of formula (II):

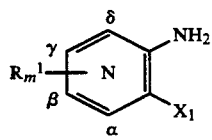

as defined in claim 1, and a compound of formula (III/C):

in which $R_3C$ is a linear or branched loweralkyl group unsubstituted or substituted with one or more halogen atoms and $X_2$ is a halogen enabling a compound of formula (I) for which

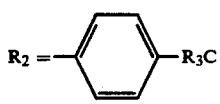

in which $R_3C$ is a linear or branched loweralkyl group unsubstituted or substituted with one or more halogen atoms to be obtained.

11. The process as claimed in claim 1 using as starting materials a compound of formula (II):

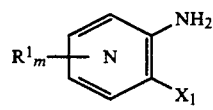

as defined in claim 1, and a compound of formula (III/D):

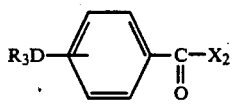

in which $R_3D$ is a linear or branched lower alkoxy group, unsubstituted or substituted with one or more halogen atoms, and $X_2$ is a halogen enabling a compound of formula (I) for which

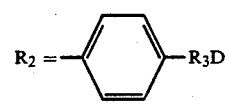

in which $R_3D$ is a linear or branched alkoxy group unsubstituted or substituted with one or more halogen atoms, to be obtained.

12. The process as claimed in claim 1 using as starting materials a compound of formula (II/B):

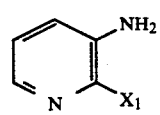

in which $X_1$ is a halogen atom, and a compound of formula (III):

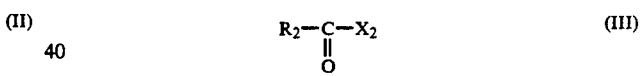

as defined in claim 1 enabling an oxazolo[5,4-b] pyridine compound of formula (I/Z):

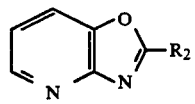

in which $R_2$ has the same meaning as given in formula (I) in claim 1 to be obtained.

13. The process of claim 10 wherein $R^3C$ is trifluoromethyl.

14. The process of claim 1, wherein $R^1$ is a trifluoromethyl group.

15. The process of claim 1, wherein $R^2$ is a 5- or 6-membered heterocycle containing one or two hetero atoms which are selected from the group consisting of oxygen, nitrogen, and sulfur, and which may be unsubstituted or substituted with a lower alkyl group or a cyano group.

16. The process of claim 1, wherein $R^3$ is a trifluoromethyl group.

17. The process of claim 1, wherein $R^3$ is a benzoylamino group which is substituted with a halogen atom selected from the group consisting of chlorine and bromine.

* * * * *

UNITED STATES PATENT AND TRADEMARK OFFICE
CERTIFICATE OF CORRECTION

PATENT NO. : 5,077,408
DATED : Dec. 31, 1991
INVENTOR(S) : Gerald Guillaumet, Christine Flouzat It is certified that error appears in the above-identified patent and that said Letters Patent is hereby corrected as shown below:

In each formula listed below (seven) (7) in all, to the far left of each formula, change the "$R_m^1$" to read -- $R^1_m$ --.
    Column 1, Formula (I), approximately line 12;
    Column 3, Formula (II), approximately line 7;
    Column 3, Formula (IV), approximately line 33;
    Column 11, Formula II, approximately line 29;
    Column 11, Formula IV, approximately line 53;
    Column 12, Formula II, approximately line 54;
    Column 13, Formula II, approximately line 41;

Column 1, approximately line 50; in the formula "$R_n^3$"
    should read -- $R^3_n$ --.
Column 5, approximately line 31; "3TM" should read -- 3-(4- --.
Column 9, line 6; "placing" should read -- replacing --.
Column 9, line 42; "-amino-2 TM chloropyridine" should read
    -- -amino-2-chloropyridine --.
Column 9, line 53/54; move the closing parenthesis from the beginning of line 54 to the end of line 53 and insert before the hyphen.
Column 10, line 32; "$R_n^3$" should read -- $R^3_n$ --.
Column 11, approximately line 48; "$R^2$ the" should read -- $R^2$ has the --.
Column 12, line 36; "which 1 is" should read -- which X1 is --.

Signed and Sealed this

First Day of June, 1993

Attest:

MICHAEL K. KIRK

*Attesting Officer*    Acting Commissioner of Patents and Trademarks